United States Patent [19]

Draenert

[11] Patent Number: 4,718,910

[45] Date of Patent: Jan. 12, 1988

[54] BONE CEMENT AND PROCESS FOR PREPARING THE SAME

[76] Inventor: Klaus Draenert, Gabriel-Maxstr. 3, 8000 Munchen 90, Fed. Rep. of Germany

[21] Appl. No.: 774,086

[22] Filed: Sep. 9, 1985

[30] Foreign Application Priority Data

Jul. 16, 1985 [DE] Fed. Rep. of Germany ....... 3525362

[51] Int. Cl.$^4$ ..................... A61L 25/00; C08L 33/06; C08K 5/09; C08K 7/00
[52] U.S. Cl. ........................................ 623/16; 623/18; 623/66; 523/114; 523/115; 523/116; 524/533; 524/853; 128/92 YQ; 433/202.1
[58] Field of Search ...................... 523/114, 115, 116; 623/16, 18; 128/92 B, 92 C; 524/853, 533

[56] References Cited

U.S. PATENT DOCUMENTS

| | | | |
|---|---|---|---|
| 3,872,047 | 3/1975 | Jandourek | 524/533 |
| 4,373,217 | 2/1983 | Draenert | 523/114 |
| 4,404,309 | 9/1983 | Masler | 524/853 |
| 4,457,878 | 7/1984 | Draenert | 623/18 |
| 4,547,390 | 10/1985 | Ashman et al. | 128/92 C |

FOREIGN PATENT DOCUMENTS

| | | | |
|---|---|---|---|
| 0041292 | 4/1976 | Japan | 523/115 |
| 0822816 | 4/1981 | U.S.S.R. | 523/115 |

*Primary Examiner*—Herbert J. Lilling
*Attorney, Agent, or Firm*—Bucknam and Archer

[57] ABSTRACT

The object of this invention is a bone cement comprising a mixture of polyacrylate and/or polymethacrylate pre-polymers, monomeric acrylic and/or methacrylic acid derivatives, a polymerization catalyst and possibly a stabilizing agent and an accelerator, and a process for the preparation and application thereof. In the bone cement of the invention, the pre-polymer is a mixture of 5–50% by weight of polyacrylate and/or polymethacrylate fibers with a length of greater than 2 mm and up to 15 mm and a thickness of 50–750 $\mu$m, and 50–95% by weight of polyacrylate and/or polymethacrylate pearl polymers consisting of 1–140 $\mu$m polymer beads, preferably between 30 and 40 $\mu$m as uniform in size as possible, the surface of which is advantageously enlarged by mechanical and/or chemical treatment. The prepolymer may also consist entirely of bead-shaped particles.

30 Claims, 1 Drawing Figure

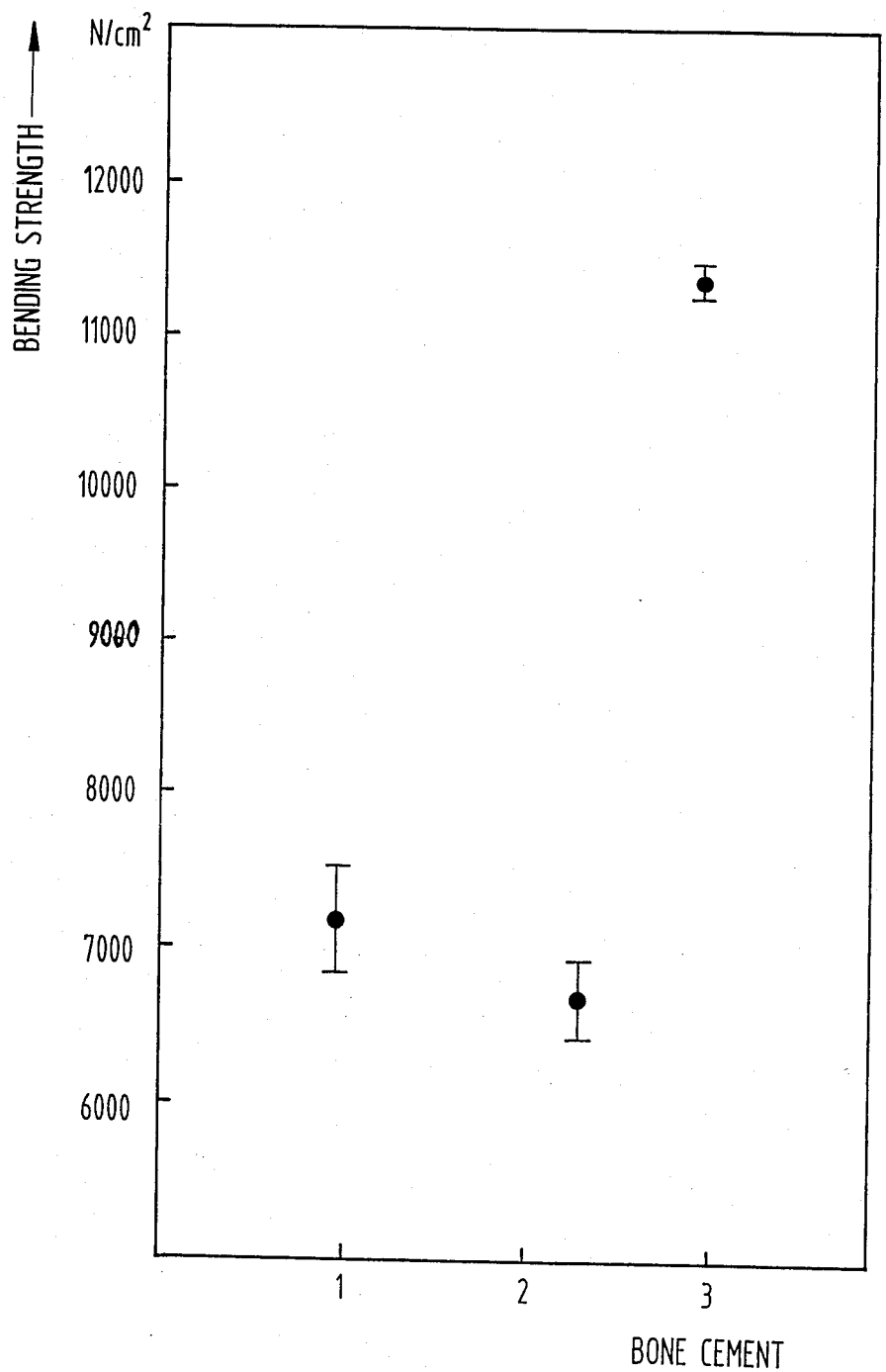

BONE CEMENT AND PROCESS FOR PREPARING THE SAME

FIELD OF THE INVENTION

The invention relates to a bone cement with a polyacrylate and/or polymethacrylate base, and/or their co-polymers, which can be used in particular as a bone replacement, bone stabilizing and prosthesis anchoring material.

DESCRIPTION OF THE RELATED ART

Known bone cements consist of a polymer component (bead-shaped acrylate or methacrylate pre-polymers termed "bead polymers" or "pearl polymers"), a monomeric acrylic or methacrylic acid derivative, e.g. methyl methacrylate, a polymerization catalyst and possibly a stabilizing and an activating agent or accelerator. Prior to use, the components are mixed to a homogeneous mass and brought to the site of application in a suitable way, e.g. by means of a cement pistol. The monomeric component hardens by polymerization and thereby encloses the pre-polymer. A homogeneous polymer structure results.

Polyacrylate-based bone cements are not absorbable. They become incorporated by ingrowth of the body's tissue are completely enclosed. A stable connection between the implant and the implant bed is given by an interlocking. To date, bonding on the molecular level has neither been proven nor demonstrated. Under favorable biomechanical conditions, however, i.e. when overloading the interface between the implant and the bone can be avoided, there is closed bone to cement contact and thus a interlocking of the implant in the bony bed.

Frequently, however, biomechanical strain on the implant, caused by the bending and shearing forces acting on the implant, leads to surface shifts with the implant acting against the implant bed (bone surface). This results in bone absorption, the rapid remodelling of lamellae to inferior bone and finally in the formation of a taut connective tissue sheath.

Due to the strain on the interface caused by bending and shearing forces, all the various stages of loosening, including the complete loosening en block of the entire implant can be observed.

There have been a number of attempts to enlarge the implant bone interface with improved methods of implantation (impactors). Attempts have also been made to substantially enlarge the surface adjacent to the implant bed by admixing absorbable materials (see DE-B-No. 29 05 878). The admixture of such fillers or filling substances has indeed enlarged the surface in a very impressive manner; bone has been shown to grow deep into the implant. However, admixing filler substances also weakens the mechanical strength of these bone cements with respect to the bending and torsion forces acting on the cement sheath enclosing the prosthesis.

The weakening of the bone cements' mechanical strength is particularly pronounced in those cements to which watery gels or soluble filling substances have been added. (See DE-A-No. 25 18 153 and J. Biomed. Mater. Res. Vol. 11 (1977), pp. 373-394).

In the final analysis, none of these bone cements exhibits the required stability to form a stable cement sheath around a prosthetic component.

Several attempts at overcoming this disadvantage have been made with fibrous cements. For example, in DE-A-No. 27 24 814 glass fibers of varying lengths were admixed and the bending strength of the bone cements immensely increased. Adding these fibers, however, led to the so-called "lattice phenomenon" with the fibers leaning up against the bony bed in the shape of a lattice and not following the cement matrix into the transversely anchoring pores of the bony bed. This resulted in a great weakening of the cement in the transverse supports which are of major importance for anchoring. The bone cements' mixing and processing capacities were also drastically reduced so that in the final analysis, bone cavity casts with these fibrous cements were the equivalent of the primary application of ceramic prostheses. The plastic transverse anchoring of the bone cements was insufficient. The fiber reinforcement with carbon fibers described in EP-A-No. 6 414 showed the same results and, for this reason, was not suited for clinical use.

SUMMARY OF THE INVENTION

It is the object of the invention to provide a bone cement of the type mentioned above which presents, on the one hand, a large surface to the implant bed and, on the other hand, sufficient mechanical strength and a closed cement sheath surrounding the prosthetic component.

It is another object of the invention to provide a process for producing this bone cement. Still another object of the invention is the use of this bone cement in the treatment of bone defects. Still another object of the invention is the use of polyacrylate and/or polymethacrylate fibers in polyacrylate-based bone cements.

The invention relates to a bone cement comprising a mixture of particulate polyacrylate and/or polymethacrylate pre-polymers, monomeric acrylic and/or methacrylic acid derivatives, a polymerization catalyst and possibly a stabilizing and an activating agent, in which the entire surface of the pre-polymer particles is enlarged by treating said particles mechanically and/or chemically and to a process for preparing this bone cement and its use in the treatment of bone defects.

The invention relates to a bone cement comprising a mixture of polyacrylate and/or polymethacrylate pre-polymers, monomeric acrylic and/or methacrylic acid derivatives, a polymerization catalyst and possibly a stabilizing and an activating agent, in which the pre-polymer is a mixture of 5-50% by weight of polyacrylate and/or polymethacrylate fibers with a length of greater than 2 mm and up to 15 mm and a thickness of 50-750μm, and 50-95% by weight of polyacrylate and/or polymethacrylate bead polymers consisting of polymer bead particles and to a process for preparing this bone cement and its use in the treatment of bone defects.

The invention is based on the surprising finding that by enlarging the surface of the bead polymer, e.g. by replacing part of the bead polymer with acrylate and/or methacrylate fibers of a specific length and thickness and/or by crushing part or all of the bead polymer and/or by chemically changing its surface, without substantially changing the mixing capacity of the cement, considerably higher mechanical stability can be achieved. Moreover, it was also found that a polymer fraction with a uniform size distribution results in a great increase in strength.

In this invention, the terms "polyacrylate" and "polymethacrylate" also include the co-polymers of the compounds named.

Useful polyacrylates and polymethacrylates are all polymers and copolymers of acrylic and methacrylic acid esters that are suitable for bone cements. The esters with aliphatic $C_1$-6-alcohols, in particular the methyl esters, are preferred.

DETAILED DESCRIPTION OF THE INVENTION

The behavior of the pearl polymer during the polymerization of the bone cements on the market has shown that the bead—the shaping element for the bone-building cell—is an important morphological component. Its very small surface, however, is not suited for the matrix compound system of the bone cement. Enlarging this surface by means of prior chemical treatment (solvents or etching agents) or mechanical crushing resulting in a polygonal configuration of the pearl fragments can greatly enhance the mechanical strength of these bone cements.

The polymer powder (pre-polymer particles) used in the invention consists of polyacrylic or polymethacrylic acid or polyacrylate or polymethacrylate or co-polymers of the abovementioned compounds.

The pre-polymer particles preferably have a grain size of between 5 and 60 $\mu m$, and even more preferably between 10 and 45 $\mu m$, with the maximum being approx. 40 $\mu m$.

The mean molecular weight of the pre-polymer particles is preferably between 100,000 and 2,000,000.

The polymer powder is treated mechanically and/or chemically prior to use in order to give the pre-polymer particles the largest possible surface.

Prior mechanical treatment involves grinding or crushing the polymer beads, preferably in a mill, e.g. a ball mill, or with a mortar to at least crush the larger polymer beads. The powder mixture then consists of complete polymer beads and crushed bead fragments or only bead fragments.

With prior chemical treatment, the polymer powder is treated with inorganic or organic solvents or substances. The surface of the polymer beads is etched or enlarged in such a way that optimal adhesion between the polymer beads and the fully polymerized monomer liquid is obtained.

Following treatment (in a ball mill, for example), the particles' size distribution is a modified Gaussian distribution. It is a particular advantage when the particles are as uniform and constant in size as possible. In this way, monomer consumption is reduced. The particles can be packed more closely geometrically. They are packed more stably and the mechanical strength of the bone cement is increased.

A particle size of approx. 30–40 $\mu m$ is particularly preferred. Such a "purified spectrum" of particles can be obtained by sifting, for example by two-fold sifting, whereby the particles which are too small and those which are too large are sifted out in separate steps. "Particle size" refers to the approximate maximum particle diameter.

Sifting out a uniform fraction of a pure bead polymer also results in increased strength and causes a drastic reduction in monomer content, which in turn has a positive effect on the bone cement's compatibility.

In the embodiment of the invention in which fibers are added to the pre-polymer, the surface of the fibers can be pretreated with inorganic or organic solvents or other substances to obtain improved adhesion between the polymer beads, the fibers and the fully polymerized monomer liquid.

The amount and size of fiber in the pearl polymer determine the mixing and implanting characteristics of the bone cements. All requirements with respect to long and short-term stability can be fulfilled for a precisely defined particle size.

These bone cements present an additional advantage: due to their greatly improved mechanical properties, they are particularly suited for contributing to a substantial enlargement of the surface at the interface when absorbable fillers, such as those described in DE-B-No. 29 05 878, are added.

The object of this invention also includes the use of polyacrylate and/or polymethacrylate or their co-polymers in the form of fibers with a length of greater than 2 mm and up to 15 mm and a thickness of 50–750 $\mu m$, preferably up to 500 $\mu m$, introduced in the form of monofils or woven to textiles; in polyacrylate-based bone cements, and the use of this bone cement in the treatment of bone defects.

In a preferred embodiment of a process of this invention, the mixing of the components is accelerated and improved by coaxial rotation, and the appearance of monomer bubbles prevented by pre-pressurizing the bone cement during the initial stages of polymerization at pressures of approx. 0.1–2 MPa, preferably 0.5–0.6 MPa as a function of the bone cement's viscosity.

The particular advantage of the implantation materials in accordance with the invention is that by replacing the bead polymer, the material as such is not changed, so that all that results is an improvement in the mechanical properties.

In the present invention, fibrous acrylate and/or methacrylate polymers are used as they are used in the fiber optics industry. Co-polymers of acrylates and methacrylates can also be used. Polymers of methyl methacrylate are preferred. These materials are known and can be prepared using known processes. These are primarily extrusion processes in which the threads are spun in precipitating baths and rolled onto spools. The threads are made in all thicknesses with various polymers and co-polymers. They are commercially available. The threads are supplied on rolls by the kilometer. A chopper can then cut them to the desired length. They are mixed with the polymer powder in ultrasonic jolters.

Adding fibers to bead polymers of the same material has the particular advantage—as has been demonstrated—that there is optimal wetting of the pre-polymer components; this could not be observed with foreign, carbon or glass fibers. Due to the nearly identical chemical structure of all components, a permanent and stable interlocking system results which does not destroy itself, nor does it behave incoherently or anisotropically as has been observed with foreign fiber systems.

The negative properties observed when foreign fibers were added were not observed with these materials of similar chemical structure.

An important advantage of the present invention is the fact that material reinforcement is achieved in the composite material, although it is homogeneous and displays similar mechanical behavior. The surprising effect of the present invention is that this could be solved advantageously. Enlarging the surface of the pre-polymer particles and mixing fibrous polyacrylates and/or polymethacrylates to the pearl polymer cause the liquid monomer to completely wet these components. Filling defects and air inclusions occur to a much lesser extent compared to observations with foreign fiber mixtures.

DE-B-No. 29 05 878 mentions the fact that in the bone cement described therein, pre-polymers are preferred which have an irregular granular shape or take the shape of flakes or fibrous cylinders. These fibrous cylinders should not exceed 1-2 mm in length. DE-B-No. 29 05 878, however, does not teach the use of a mixture of pre-polymers of varying external shape, e.g. bead polymers and fibrous polymers, or the desired enlargement of the pre-polymer particles' surface by means of mechanical or chemical treatment, in particular the selection of a uniform particle size.

In has been shown that a fiber length of up to 2 mm does not result in an increase in the bone cement's bending or torsional strength. Compared to these short fibrous cylinders, polymer beads achieve tighter packing, so that—on the contrary—a loss of mechanical strength, in particular bending strength, can be observed when short threads are added.

Moreover, experiments have shown that a pure thread polymer leads to a drastic worsening of the bone cement's mixing and application capacity. Biological studies have shown that when compared with thread polymers, pearl polymers present superior shaping properties with respect to osteoblasts, the bone-building cells. The success aimed at in this invention occurs when a mixture of bead polymers and fiber additives is used. The fibers are not effective unless they present a minimum length of greater than 2 mm. Fibers with a length of up to 40 mm can be added. The optimal material characteristics are obtained with a fiber length of between 3 and 8 mm, and in particular between 3 and 4 mm, with a thickness of between 100 and 300 $\mu$m, preferably 200 $\mu$m. By varying the mixture, bone cements closely related to their strength characteristics can be prepared which exhibit all sorts of mixing and application capacities. The size of the polymer beads in the bead polymers ranges from 1-140 $\mu$m, preferably from 5-60 $\mu$m and even more preferably from 10-45 $\mu$m. A particularly preferable embodiment, also when fibers are added, is a uniform particle size of approx. 40 $\mu$m.

This variability in the preparation of bone cements has great advantages, especially since today various principles are followed for anchoring the prosthetic components.

In conventional joint replacement components, the prosthetic components are anchored in the bone with the bone cement, i.e. the joint components are completely surrounded by bone cement which anchors them over a large surface in the bony bed. In recent years, prosthetic components have been developed which can selflock—without adding bone cement—in the implant bed. These so-called self-locking or straight shaft prostheses cannot get along without bone cement, however, for locking in a physiologically curved femur, for instance, is only possible at two or three points. Thus, rotation instability or instability in the sagittal direction remains. To overcome this instability, all self-locking straight shaft prostheses are preferably anchored with bone cement in the bony bed. Due to the very thin cement sheath at at least three sites, these bone cements must meet very high material requirements. Cements to which a large amount of acrylate fiber has been added are particularly suited for this purpose because of their high bending and torsional strength.

When fibers are added, the pre-polymer used in accordance with the invention consists of 5-50, preferably 15-45 and more preferably 20-40% by weight of fibrous components. In the bone cement in accordance with the invention, the weight ratio of pre-polymer to monomeric components is 50:50 to 80:20, preferably 60:40 to 70:30. As the polymerization catalyst, stabilizing agent and accelerator the substances normally used in bone cements are added. A specific example of an appropriate catalyst is dibenzoyl peroxide; a stabilizing agent: hydroquinone; and an accelerator: N,N-dimethyl-p-toluidin.

5-35% by weight, based on the mass of the pre-polymer and the monomer, of absorbable tricalcium phosphate with a particle size of between 50 and 100 $\mu$m and an available pore volume of less than 0.1 ml/g can be added to the bone cement of the invention. The type of tricalcium phosphate used and the effect obtained have been described in DE-B-No. 29 05 878.

An antibiotic can also be added to the implantation material of the invention to avoid infections in the implant and the implant bed. Infections can never be excluded even when working carefully under aseptic conditions. They generally occur via hematogenous spread since the implant takes germs from the body's defense. Gentamicin, with which very good results have been obtained, is a preferred antibiotic. The use of gentamicin in bone cements is known from DE-A-No. 20 22 177, for example. However, it was not obvious to add gentamicin to the fiberenforced bone cement of this invention since, as can be seen in the literature, the addition of all filling substances must lead to a mechanical weakening of the cements, and the objective of these fiber cements was to improve the mechanical strength. It has been found that adding up to 6 g gentamicin to 40 g cement powder causes no major changes in the material properties of the bone cements of the invention. This is due to the highly elastic properties of these substances. Gentamicin admixtures of between 1 and 4% by weight led to no changes whatsoever in the mechanical parameters.

Other substances, such as "bone morphogenetic protein" can also be added to the bone cement of the invention. The basic substance of this protein can be obtained from animals' bones. In this way, a bioactivation of the bone cements can be achieved in such a way that even small additions, distributed homogeneously in the cement, lead to a considerable acceleration of growth into bone. Additions of between 0.01 and 2% by weight do not change the bone cement's mechanical properties.

Additional admixtures can include all types of chemotherapeutic substances such as cytostatic agents and other antibiotics, as well as the hormone calcitonin. Of the numerous antibiotics to be considered, those which are not damaged at the temperatures occurring during polymerization should be mentioned: erythromycin, lyncomycin, clyndamycin, novobiocin, vancomycin, fusidin acid, rifampicin, polymycine, neomycin, kanamycin and tobramycin.

Air inclusions and polymerization bubbles can be avoided to a large extent by pre-pressurizing the cement. The mixing of the bone cements can be improved in this way since the wetting of the pre-polymer can be greatly improved due to the co-axial rotation. If this rotation is performed prior to pre-pressurization the air embedded in the cement mixture can be completely removed with an appropriate air evacuation means. The mixture is then pre-compressed at pressures of between 0.1 and 2 MPa, preferably 0.5–0.6 MPa. After the fourth minute of mixing and after the pressure has fallen, the cements are applied to the implant bed; the pressure in the piston is increased gradually. Bone cements prepared in this way exhibit not only greatly improved matrial properties; morphologically, they also display considerably fewer bubble inclusions. In certain cases, they can be similar to industrial plexiglas.

The present invention has shown that a mixture of pearl polymers and fiber polymers can become biologically active, since the morphological equivalent of an osteoblast—the bone-building cell—is a 20—40 $\mu$m bead. The bone cements' shearing and torsion strength can be substantially improved by partially weaving polymer fibers to textiles cut into pieces which are 2–15 mm in length. This strength is of particular importance for the strain on the cement sheath.

In addition to the reinforcement achieved with polymer fibers, a bone cement's mechanical strength can be increased in accordance with this invention by grinding the polymer components in a ball mill before they are added to the monomer. If the grinding process is performed for a sufficiently long period of time, a very narrow size spectrum of small polymer beads (diameter: approx. 40 $\mu$m) is obtained since the beads with a larger diameter are crushed to fragments during the grinding process. This mixture of polymer fragments and beads of a small diameter is then added to the monomer and the cement is mixed in the conventional manner.

Using polymer beads of approximately the same size is a particular advantage. This is best achieved by repeatedly sifting the particles in standard-sized sieves. The difference in the sieves' mesh size should be dept as small as possible to obtain—ideally—polymer beads of equal diameter. The mechanical strength of a bone cement with this polymer component is improved by at least 20% compared to conventional cements.

The bending test shown in the figure compares the bending strength of the bone cement of the invention with that of commercial bone cements under identical conditions (Palacos R ®, trade n , F. Merck, Darmstadt, Federal Republic of Germany; Sulfix-6 ®, trade name, Sulzer Bros., Winterthur, Switzerland).

For the bending test, standard cylinder-shaped samples of the bone cement in accordance with the invention are prepared.

These samples are prepared under clinical conditions with a brief mixing phase followed by a compression phase of approx. 1–2 min.

The preparation of these samples will be described in detail in the following five examples.

EXAMPLE 1

6 g of a commercial polymethyl methacrylate co-polymer are mixed with 4 g of cut polymethyl methacrylate fibers with a thickness of 125 $\mu$m and an average length of 4 mm. This mixture is then stirred with a wooden spatula in a plastic bowl containing 4 ml of monomer (methyl methacrylate, activating agent, stabilizing agent). When the mixture is homogeneous, it can be filled in a 5 ml disposable syringe; the piston is pressed in under moderate pressure. The syringe is then placed in a pressure chamber. After closing the chamber, compressed gas is used to apply a pressure of 0.5 MPa for 2 min. After the pressure has fallen, the cement sample is left in the syringe to harden at room temperature.

EXAMPLE 2

8 g of a commercial polymethyl methacrylate pearl polymer are mixed with 2 g of polymethyl methacrylate fibers (thickness: 125 $\mu$m; length: 3–4 mm) and then added to 5 ml of monomer methyl methacrylate, activating agent, stabilizing agent). The mixture is then stirred in a plastic bowl with a wooden spatula until it is sufficiently homogeneous. This mixture can then be filled in a 5 ml disposable syringe; the piston is pushed in and the syringe placed in a pressure chamber and subjected to a pressure of 0.5 MPa for 2 min.

Following the compression phase, the cement sample is left to harden at room temperature.

EXAMPLE 3

7 g of a commercial polymethyl methacrylate pearl polymer are mixed with 3 g of cut polymethyl methacrylate fibers (thickness: 125 $\mu$m; length: 5–15 mm) and added to 4 ml of monomer (methyl methacrylate, activating agent, stabilizing agent). This mixture can then be stirred in a 20 ml disposable syringe until said mixture is homogeneous (approx. 1 min). After expanding the syringe opening, the mixture is pressed into a 5 ml disposable syringe. Said syringe is then placed in a pressure chamber and a pressure of 0.5 MPa is applied. The compression phase lasts approx. 2 min. After the pressure has fallen, the cement sample is left in the syringe to harden.

EXAMPLE 4

10 g of a commercial polymethyl methacrylate co-polymer are ground in a high-speed ball mill for 2 h. The diameter of the ground beads is 2.06 cm. This polymer is then added to 5 ml of monomer (methyl methacrylate, activating agent, stabilizing agent) in a plastic bowl. It is stirred until the mixture is homogeneous. The cement mass can then be filled in a 5 ml disposable syringe; the sample is compressed in a pressure chamber with compressed gas at 0.5 MPa for 2 min. The pressure then falls and the cement sample hardens at room temperature in the syringe.

EXAMPLE 5

Approx. 100 g of a commercial polymethyl methacrylate co-polymer are sifted for several hours on a jolter through three standard sieves with mesh widths of 40 $\mu$m, 38 $\mu$m and 36 $\mu$m. The sieves are arranged one above the other. 10 g are taken from the 38–40 $\mu$m fraction and stirred with 5 ml of monomer (methyl methacrylate, activating agent and stabilizing agent) until a homogeneous mass is formed. The cement can then be filled in a 5 ml disposable syringe and placed in a pressure chamber. It is then compressed for 2 min at a pressure of 0.5 MPa. The pressure then falls and the cement sample hardens at room temperature in the conventional manner.

The two processes in accordance with examples 4 and 5, i.e. grinding in a ball mill and sifting in standard sieves, can be combined very well to further improve the cement's strength.

The samples prepared according to the processes described above are subjected to bending stress on a universal testing machine. The test conditions were identical for all measurements.

The results of the bending test show that the bone cement of the invention displays strengths which are far greater than those observed for bone cements on the market. For example, the strength determined in the bending test for the bone cement prepared in Example 3 was 11,339 N/cm$^2$.

BRIEF DESCRIPTION OF THE DRAWING The figure presents this value graphically in comparison to the bending strengths of known bone cements. Values No. 1 and No. 2 relate to known bone cements. Value No. 1 relates to Palacos R ®, value No. 2 relates to 6 ®. Value No. 3 relates to the bone cement of the invention according to Example 3. The peak values obtained with the bone cements of the invention approach the bending strengths of pure plexiglas.

The mixing capacity of the cement described above does not differ from that of commercial bone cements. The processing and hardening phases are also comparable.

What is claimed is:

1. A bone cement consisting essentially of a mixture of component (a) and component (b), said component (a) is particles of a prepolymer which is a bead-shaped polyacrylate, a methacrylate prepolymer or mixtures thereof, said prepolymer particles having been treated prior to mixing with said component (b) mechanically by crushing said bead-shaped particles to polymorphous fragments or chemically by treatment with an inorganic or organic solvent to etch the surface and to increase the specific surface thereof or both mechanically and chemically to increase their specific surface, said component (b) is monomeric acrylic acid, monomeric methacrylic acid, derivatives thereof or mixtures thereof, and (c) a polymerization catalyst.

2. The bone cement according to claim 1, which additionally contains a stabilizing agent or an accelerator or a mixture thereof.

3. The bone cement according to claim 1, wherein the particle size of the bead-shaped prepolymer particles after crushing ranges from 1 to 140 μm.

4. The bone cement according to claim 3, wherein the particle size ranges from 10 to 45 μm.

5. The bone cement according to claim 4, wherein the particle size is uniform and is between 30 and 40 μm.

6. The bone cement according to claim 1, which includes a pharmaceutical agent which is a member selected from the group consisting of gentamicin and a bone morphogenetic protein and mixtures thereof.

7. The bone cement according to claim 1, which contains 5 to 35% by weight, based on the total weight of said prepolymer and said monomer of absorbable tricalcium phosphate with a particle size ranging from 50 to 300 μm and an available pore volume of less than 0.1 ml/g.

8. Process for preparing a bone cement which consists of treating a polyacrylate or a polymethacrylate prepolymer or mixtures thereof, consisting of polymer bead particles mechanically by crushing said bead-shaped particles or chemically by treatment with an inorganic or organic solvent to etch the surface or both mechanically and chemically to yield polymorphous particles of increased specific surface, adding thereto a monomeric acrylic or methacrylic acid, derivatives thereof or mixtures thereof to obtain a mass and homogeneously mixing said mass with a polymerization catalyst.

9. The process according to claim 8 wherein at least one of a stabilizing agent and an accelerator is added to said mass.

10. The process according to claim 8, wherein a fraction of said prepolymer particles of uniform size of 30–40 μm is sifted out prior to mixing with said monomer.

11. A method of treating a bone defect wherein a bone is replaced or stabilized or a prosthetic structure is anchored in the bone with a bone cement, which consists of replacing said bone, stabilizing said bone or anchoring said prosthetic structure into the bone with a bone cement consisting essentially of a mixture of component (a) and component (b), said component (a) is particles of a prepolymer which is a bead-shaped polyacrylate, a methacrylate prepolymer or mixtures thereof, said prepolymer particles having been treated prior to mixing with said component (b) mechanically by crushing said bead-shaped particles to polymorphous fragments or chemically by treatment with an inorganic or organic solvent to etch the surface and to increase the specific surface thereof or both mechanically and chemically to increase their specific surface, said component (b) is monomeric acrylic acid, monomeric methacrylic acid, derivatives thereof or mixtures thereof, and (c) a polymerization catalyst.

12. A bone cement consisting essentially of a mixture of (a) a prepolymer which consists of 5–50% polyacrylate fibers, methacrylate fibers or mixtures thereof, of length greater than 2 mm up to 15 mm and thickness 50–750 μm and 50–95% of a polyacrylate bead polymer or polymethacrylate bead polymer or mixtures thereof, (b) monomeric acrylic acid, monomeric methacrylic acid, derivatives thereof or mixtures thereof, and (c) a polymerization catalyst.

13. The bone cement according to claim 12, which contains a stabilizing agent, an accelerator or mixtures thereof.

14. A bone cement according to claim 12 wherein said polyacrylate and polymethacrylate fibers are in the form of monofils or are pieces of woven textiles of 2–15 mm length.

15. The bone cement according to claim 12, wherein the surface of at least one of the bead particles and the polyfibers has been treated chemically or mechanically in order to increase the specific surface thereof.

16. The bone cement according to claim 15, wherein said bead particles are mechanically treated by crushing the bead particles to polymorphous fragments.

17. The bone cement according to claim 15, wherein the bead particles and fibers are chemically treated, said bead particles and fibers have a surface, the surface is modified morphologically.

18. The bone cement according to claim 12, wherein the particles size of said prepolymer ranges from 1 to 140 μm.

19. The bone cement according to claim 18, wherein the particle size ranges from 5 to 60 μm.

20. The bone cement according to claim 19, wherein the particle size ranges from 10 to 45 μm.

21. The bone cement according to claim 20, wherein the particle size is uniform and is between 30 and 40 μm.

22. The bone cement according to claim 12, which includes a pharmaceutical agent which is a member selected from the group consisting of gentamicin and a bone morphogenetic protein and mixtures thereof.

23. The bone cement according to claim 12, which contains 5 to 35% by weight, based on the total weight of said prepolymer and said monomer, of absorbable tricalcium phosphate with a particle size ranging from 50 to 300 μm and an available pore volume of less than 0.1 ml/g.

24. The process for preparing a bone cement which consists of adding 5 to 50% by weight of a prepolymer of a polyacrylate fibers, polymethacrylate fibers or mixtures thereof with a length greater than 2 mm and up to 15 mm and a thickness of 50 to 750 μm in the form of monofils or pieces of woven textiles of 2-15 mm length and 50 to 95% by weight of a polyacrylate bead polymer or a polymethacrylate bead polymer or mixtures thereof, said bead particles being 1 to 140 μm in size to monomeric acrylic acid, methacrylic acid, derivatives thereof or mixtures thereof, to obtain a mass and homogeneously mixing said mass with a polymerization catalyst.

25. The process according to claim 24, wherein said mass is mixed with at least one of a stabilizing agent or an accelerator.

26. The process according to claim 24, wherein said polymer bead particles ar echemically or mechanically treated before adding them to said monomer whereby their specific surface is increased.

27. The process according to claim 24, wherein a fraction of bead particles of uniform size of 30-40 μm is sifted prior to adding to said monomer.

28. A method of treating a bone defect wherein a bone is replaced or stabilized or a prosthetic structure is anchored in the bone with a bone cement, which consists of replacing said bone, stabilizing said bone or anchoring said prosthetic structure into the bone with a bone cement consisting essentially of a mixture of (a) a prepolymer which consists of 5-50% polyacrylate fibers, methacrylate fibers or mixtures thereof, of length greater than 2 mm up to 15 mm and thickness 50-750 μm and 50-95% of a polyacrylate bead polymer or a polymethacrylate bead polymer or mixtures thereof, (b) monomeric acrylic acid, monomeric methacrylic acid, derivatives thereof or mixtures thereof, and (c) a polymerization catalyst.

29. The bone cement according to claim 1, wherein said polyacrylate and methacrylate prepolymers are polymers and copolymers thereof from esters of acrylic acid and methacrylic acid with an aliphatic alcohol of 1 to 6 carbon atoms.

30. The bone cement according to claim 12, wherein said polyacrylate and methacrylate prepolymers are polymers and copolymers thereof from esters of acrylic acid and methacrylic acid with an aliphatic alcohol of 1 to 6 carbon atoms.

* * * * *